(12) United States Patent
Hettche et al.

(10) Patent No.: US 7,557,240 B2
(45) Date of Patent: Jul. 7, 2009

(54) METHOD FOR THE PRODUCTION OF OPTICALLY ACTIVE ALKYL SUCCINIC ACID MONOALKYL ESTERS

(75) Inventors: Frank Hettche, Weinheim (DE); Christoph Jäkel, Limburgerhof (DE); Marko Friedrich, Lorsch (DE); Rocco Paciello, Bad Dürkheim (DE)

(73) Assignee: BASF Aktiengesellschaft (DE)

( * ) Notice: Subject to any disclaimer, the term of this patent is extended or adjusted under 35 U.S.C. 154(b) by 197 days.

(21) Appl. No.: 11/571,725

(22) PCT Filed: Jul. 6, 2005

(86) PCT No.: PCT/EP2005/007289

§ 371 (c)(1),
(2), (4) Date: Jan. 5, 2007

(87) PCT Pub. No.: WO2006/002999

PCT Pub. Date: Jan. 12, 2006

(65) Prior Publication Data

US 2008/0058547 A1     Mar. 6, 2008

(30) Foreign Application Priority Data

Jul. 7, 2004    (DE) ................ 10 2004 032 968
Feb. 18, 2005   (DE) ................ 10 2005 007 750

(51) Int. Cl.
*C07C 69/34* (2006.01)

(52) U.S. Cl. .................................... 560/190

(58) Field of Classification Search ............. None
See application file for complete search history.

(56) References Cited

U.S. PATENT DOCUMENTS

| 4,652,657 A | 3/1987 | Broger et al. |
| 5,177,220 A | 1/1993 | Schafer et al. |
| 6,043,396 A | 3/2000 | Sturmer et al. |

FOREIGN PATENT DOCUMENTS

| EP | 0158875 A2 | 10/1985 |
| EP | 0437690 A2 | 7/1991 |
| EP | 0889048 A1 | 1/1999 |
| EP | 1127061 B1 | 8/2001 |

OTHER PUBLICATIONS

Burk et al (Angewandte Chemie, International Edition, Practical Access to 2-Alkylsuccinnates Through Asymmetric Catalytic Hydrogenation of Stobbe-Derived Itaconates, 1998, 37(13/14), pp. 1931-1933.*
Holz, J. et al., "Synthesis of a New Class of Functionalized Chiral Bisphospholane Ligands and the Application in Enantioselective Hydrogenations," J. Org. Chem., 1998, vol. 63, pp. 8031-8034.
Wu, S. et al., "Synthesis of *Ortho*-phenyl Substituted MeO-BIPHEP Ligand and its Application in RH-catalyzed Asymmetric Hydrogenation," Tetrahedron Asymmetry, 2004, vol. 15, pp. 2177-2180.
Carmichael, D. et al., "Hybrid P-chiral Diphosphines for Asymmetric Hydrogenation," Chem. Commun., 1999, vol. 261, pp. 261-262.
Achiwa, K. et al., "The Mechanism of Asymmetric Hydrogenations Catalyzed by Chiral Pyrrolidinephosphine-Rhodium Complexes," Tetrahedron Lett., 1978, No. 47, pp. 4683-4686.
Christopfel, W. C. et al., "Catalytic Asymmetric Hydrogenation with a Rhodium (I) Chiral Bisphosphine System. A Study of Itaconic Acid and Some of Its Derivatives and Homologues," Journal of the American Chemical Society, vol. 101, No. 15, pp. 4406-4408.
Saito, S. et al., "Syntheses of Novel Sugar Phosphine Derivatives, and Homogeneous Hydrogenation Reactions with Their Rhodium Complexes," Chem. Pharm. Bull., 1985, vol. 33, No. 12, pp. 5284-5293.
Kawano, H. et al., "Ruthenium (II)-Binap Complex catalyzed Asymmetric Hydrogenation of Unsaturated Dicarboxylic Acids," Tetrahedron Letters, 1987, vol. 28, No. 17, pp. 1905-1908.
Kawano, H. et al., "Asymmetric Hydrogenation of Prochiral Alkenes Catalysed by Ruthenium Complexes of (R)—(+)—2,2'—Bis(disphenylphosphino)—1,1'—binaphthyl," J. Chem. Soc., 1989, vol. 1, pp. 1571-1575.
Ostermeier, M. et al., "Highly Enantioselective Rhodium-Catalyzed Hydrogenation of 2-(2_Methoxy-2-oxoethyl)acrylic Acid- A Convenient Access of Enantiomerically Pure Isoprenoid Building Blocks," Eur. J. Org. Chem., 2003, pp. 3453-3459.
Devi, A. R. et al., "An Efficient a Regiospecific Esterification of Dioic Acids Using PTSA," Indian Journal of Chemistry, 2000, vol. 39B, pp. 294-296.
Anand, R. C. et al., "Selective Esterification of Nonconjugated Carboxylic Acids in the Presence of Conjugated or Aromatic Carboxylic Acids Under Mild Conditions," J. Chem. Research, 1999, pp. 378-379.
Ram, R.N. et al., "Selective Esterification of Aliphatic Nonconjugated Carboxylic Acids in the Presence of Aromatic or Conjugated Carboxylic Acids catalysed by $NiCl_2.6H_2O$," Tetrahedron, 1997, vol. 53, No. 21, pp. 7335-7340.
Uson, R. et al., "Cationic Iridium(I) Complexes with 1,5-Cyclooctadiene and Nitrogen Ligands," Inorganica Chimica Acta, 1983, vol. 73, pp. 275-279.

* cited by examiner

*Primary Examiner*—Paul A Zucker
(74) *Attorney, Agent, or Firm*—Connolly Bove Lodge & Hutz LLP

(57) ABSTRACT

The invention relates to a process for preparing optically active alkylsuccinic acid monoalkyl esters of the formula (I)

where D and E are independently of one another H, $C_1$-$C_{10}$ alkyl, R is $C_1$-$C_{10}$ alkyl, aryl or alkylaryl.

12 Claims, No Drawings

METHOD FOR THE PRODUCTION OF OPTICALLY ACTIVE ALKYL SUCCINIC ACID MONOALKYL ESTERS

RELATED APPLICATIONS

This application is a national stage application (under 35 U.S.C. 371) of PCT/EP2005/007289 filed Jul. 6, 2005, which claims benefit of German application 102004032968.0 filed Jul. 7, 2004 and German application 102005007750.1 filed Feb. 18, 2005.

The invention relates to a novel process for preparing optically active alkylsuccinic acid monoalkyl esters.

PRIOR ART

A direct selective access to systems of type III and their optical antipodes

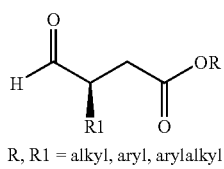

R, R1 = alkyl, aryl, arylalkyl by asymmetric hydrogenation starting from their direct unsaturated precursors has not to date been satisfactorily achieved.

This is evident for example from the preparation of (2R)-methylsuccinic acid 4-methyl ester 4 from itaconic acid monomethyl ester 3, which can easily be obtained at low cost.

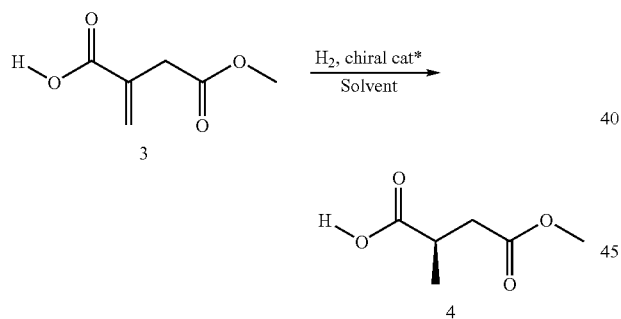

K. Achiwa, Y. Ohga, Y. Itaka, *Tetrahedron Lett.* 1978, 19, 4683 obtain compound 4 with 60% enantiomeric excess (=ee=[content of enantiomer 1—content of enantiomer 2]/[content of enantiomer 1+enantiomer 2]) in methanol.

W. C. Christopfel, B. D. Vineyard, *J. Am. Chem. Soc.* 1979, 101, 4406 obtain compound 4 with 55% ee in methanol.

S. Saito, Y. Nakamura, Y. Morita, *Chem. Pharm. Bull.* 1985, 33, 5284 obtain compound 4 with 90% ee in benzene/MeOH 1/4.

H. Kawano, Y. Ishii, T. Ikariya, M. Saburi, S. Yoshikawa, *Tetrahedron Lett.* 1987, 28, 1905 obtain compound 4 with 60% ee in toluene/THF.

D. Carmichael, H. Doucet, J. M. Brown, *Chem. Commun.* 1999, 261 H. Kawano, T. Ikariya, Y. Ishii, M. Saburi, S. Yoshikawa et al., *J. Chem. Soc. Perkin Trans.* 1 1989, 1571 obtain compound 4 with 94% ee in methanol.

U. Berens, M. Burk, A. Gerlach (WO 00/27855; EP 1 127 061 B1) obtain compound 4 with 95% ee in methanol.

The optical purity achieved in the processes mentioned therefore does not comply, without additional enrichment steps, with the requirements in the active ingredient sector, which are in most cases for an enantiomeric excess of $\geq 98\%$ ee.

Other processes leading to a higher optical purity either use large amounts of catalyst, i.e. a low substrate/catalyst ratio (s/c), which is uneconomic for industrial production, or the chosen reaction conditions (especially solvent) are problematic from environmental viewpoints or for reasons of occupational safety.

M. Ostermeier, B. Brunner, C. Korff, G. Helmchen, *Eur. J. Org. Chem.* 2003, 3453 obtain compound 4 with an s/c ratio of 200/1 with 97.3% ee in dichloromethane, and in $C_6H_5CF_3$, likewise with an s/c of 200/1, an ee of 98.3% is achieved. In dichloroethane, a purity of 99.3% ee is reached with an s/c ratio of 1000/1.

For the abovementioned reasons, all these processes are unsuitable for a one-stage direct synthesis on the industrial scale of optically active succinic acid alkyl esters from their olefinic precursors which can be obtained easily at low cost.

Statement of Object

The object therefore was to provide a novel process for preparing optically active alkylsuccinic acid monoalkyl esters which achieves, with small amounts of catalyst (s/c$\geq$20 000/1) and, at the same time, environmentally compatible reaction conditions, a complete conversion in the reaction and high optical yield ($\geq$98% ee), so that an efficient, environmentally acceptable, cost-efficient industrial synthesis is made possible.

DESCRIPTION OF THE INVENTION

We have found a process for preparing optically active alkylsuccinic acid monoalkyl esters of the formula (I)

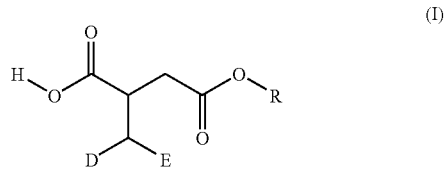

where D and E are independently of one another H, $C_1$-$C_{10}$ alkyl,

R is $C_1$-$C_{10}$ alkyl, aryl or alkylaryl, by enantioselective hydrogenation of a compound of the formula (II)

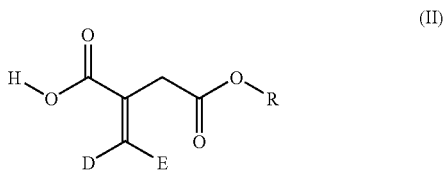

where D, E and R have the abovementioned meanings, in the presence of a catalyst which includes a phospholane ligand of the formula (L)

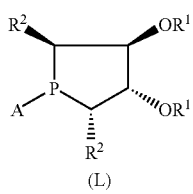

(L)

where:
R¹ and R² are independently of one another $C_1$-$C_6$ alkyl, aryl, alkylaryl,
R¹ is additionally hydrogen,
A is either R¹ or

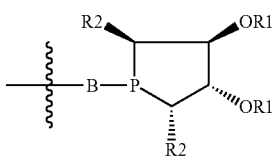

with B=a linker with 1-5 C atoms between the two P atoms or Cp-Fe-Cp.

The compounds of the formula (I) are optically active compounds which are intended in each case to represent one enantiomer (R or S).

Enantioselective hydrogenation is intended to mean hereinafter that the hydrogenation does not result in both enantiomers to the same extent, but that one enantiomer (R or S) is formed in high optical purity, in particular with an ee of 98, 99, 99.5%.

The starting compounds of the formula (II) are known from the literature and can easily be prepared by conventional methods (for D=E=H; R=Me see, for example, A. R. Devi, S. Rajaram, *Ind. J. Chem* 2000, 39B, 294-296 or R. C. Anand, V. A. Mihotra, *J. Chem. Res*. (S) 1999, 378-379 or R. N. Ram, I. Charles, *Tetrahedron* 1997, 53, 7335-7340). Preferred starting compounds (II) are those in which D and E have independently of one another the meaning of H, methyl, ethyl, propyl, butyl, pentyl, hexyl, heptyl, octyl, nonyl, decyl, where the alkyl name includes both the unbranched and the branched isomers. Particularly preferred starting compounds are those in which D and E are H and methyl, especially those in which D and E are H or D and E are methyl. Further preferred starting compounds (II) are those in which D is H and E is butyl.

The radical R may be $C_1$-$C_{10}$ alkyl, where individual H atoms of the alkyl radical may in turn be replaced by other radicals such as OH, $NH_2$, $NO_2$, CN, F, Cl, Br, I. In addition, R may also be aryl radicals such as phenyl, naphthyl, and alkylaryl radicals such as benzyl, where the aryl radicals may also in turn be substituted. Preferred radicals R are methyl, ethyl, propyl, i-propyl and tert-butyl. R is particularly preferably methyl.

The catalysts consist of a metal atom of the group Pd, Pt, Ru, Rh, Ni, Ir. Particularly preferred catalysts have Rh, Ru or Ir as metal atom, and Rh catalysts are particularly suitable for the process of the invention.

Metal sources which can preferably be used to prepare the catalysts are precursors such as, for example, $Pd_2(DBA)_3$, $Pd(Oac)_2$, $[Rh(COD)Cl]_2$, $[Rh(COD)_2]X$, $Rh(acac)(CO)_2$, $RuCl_2(COD)$, $Ru(COD)(methallyl)_2$, $Ru(Ar)Cl_2$, Ar=aryl, both unsubstituted and substituted, $[Ir(COD)Cl]_2$, $[Ir(COD)_2]X$, Ni(allyl)X. It is also preferable to use NBD (=norbornadiene) instead of COD (=1,5-cyclooctadiene).

X can in these cases be any anion which is known to the skilled worker and can be used generally in asymmetric synthesis. Examples of X are halogens such as $Cl^-$, $Br^-$, $I^-$, $BF_4^-$, $ClO_4^-$, $SbF_6^-$, $PF_6^-$, $CF_3SO_3^-$, $BAr_4^-$. X is preferably $BF_4^-$, $CF_3SO_3^-$, $SbF_6^-$, $ClO_4^-$, especially $BF_4^-$ and $CF_3SO_3^-$.

The catalysts of the process of the invention additionally comprise one or more phospholane ligands of the general formula (L). Preferred substituents R¹ and R² are H, methyl, ethyl, n-propyl, isopropyl, n-butyl, isobutyl, tert-butyl, benzyl. The substituent combination of R¹=H and R²=methyl is particularly preferred.

Also preferred in addition are the R¹ radicals in which the two R¹ form a bridge, such as, for example, isopropylidene or benzylidene.

In the case of diphospholanes, preference is given to those in which

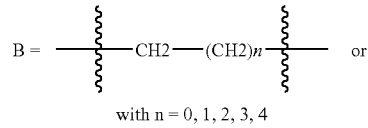

with n = 0, 1, 2, 3, 4

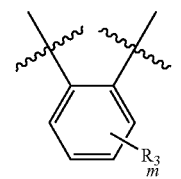

with m = 0, 1, 2, 3
R3 = alkyl or fused aryl

Particularly preferred linkers B are those in which n=1 or 2 or m=0.

Preferred ligands L are those in which A represents a further phospholane residue together with a linker B, where B may represent a bridge of 1 to 5 C atoms between the two phosphorus atoms. The expression 1-5 C atoms between the two phosphorus atoms does not mean that B consists of a maximum of 5 C atoms, but that the direct connection between the two P atoms comprises not more than 5 C atoms. B can be for example a phenyl ring if the two P atoms are linked thereto in ortho positions.

The linker B can, however, also be a ferrocene-type compound consisting of substituted or unsubstituted cyclopentadienyl radicals (Cp) which comprise an Fe atom in sandwich fashion (Cp-Fe-Cp), where the P atoms are bonded to the Cp radicals.

Particularly preferred ligands L are:

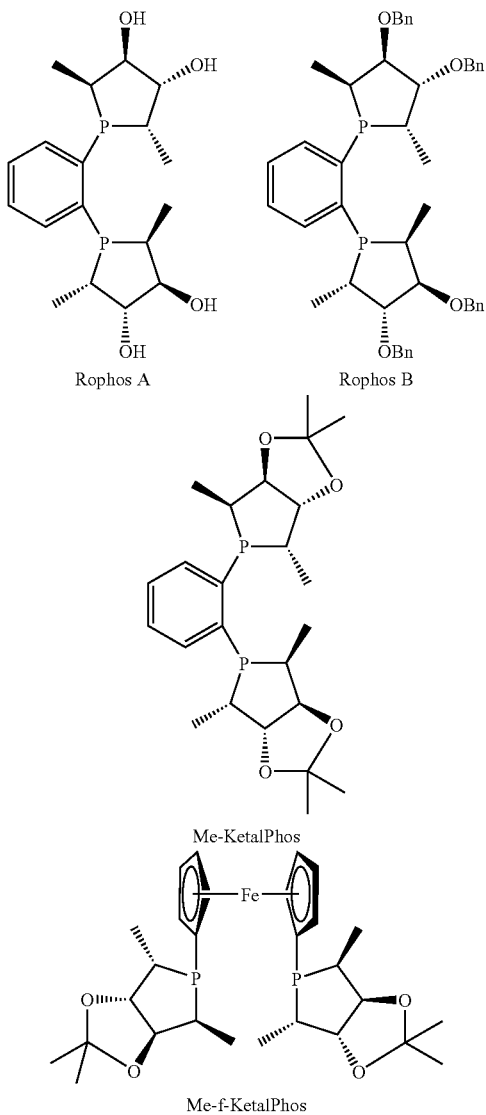

The invention comprises not only the enantiomers depicted by these formulae but also their optical antipodes.

For the preparation of the Rophos catalysts, reference is made to EP 0 889 048, which is incorporated herein by reference.

Ligand-metal complexes can be prepared by synthesizing catalytically active complexes in known manner (e.g. Uson, Inorg, Chim. Acta 73, 275 1983, EP-A 0158875, EP-A 437690) by reaction with rhodium, iridium, ruthenium, palladium, platinum, nickel complexes which comprise labile ligands (e.g. $[RuCl_2(COD)]_n$, $[Rh(COCD)_2]BF_4$, $[Rh(COD)_2]CF_3SO_3$, $Rh(COD)_2ClO_4$, $[Ir(COD)Cl]_2$, p-cymene ruthenium chloride dimer). NBD can also be employed instead of COD for preparing the complexes with good results.

As the skilled worker is aware, the complex (=precatalyst) can be generated before use and be isolated and then employed "ready to use", or be generated in situ in the reaction vessel before the actual hydrogenation (see below).

Suitable solvents are all solvents known to the skilled worker for asymmetric hydrogenation. Preferred solvents are lower alkyl alcohols such as methanol, ethanol, isopropanol, and toluene, THF, ethyl acetate. Methanol is particularly preferably employed as solvent in the process of the invention.

The hydrogenation of the invention is normally carried out at a temperature of from −20 to 150° C., preferably at 0 to 100° C. and particularly preferably at 10-80° C.

The hydrogenation of the invention uses substrate/catalyst ratios s/c of $\geq$20 000/1 and, in such cases, results in $\geq$98% ee. Even with an s/c of 110 000/1, an ee of 98% is achieved.

Catalyst usage can be reduced even further by suitable immobilization of the catalyst.

The hydrogen pressure can be varied within a wide range between 0.1 bar and 300 bar for the hydrogenation process of the invention. Very good results are obtained in a pressure range of 1-200 bar, preferably 1-100 bar.

The reaction mixture is worked up by procedures known to the skilled worker. The product can, for example, be converted into a carboxylate, precipitated and thus removed from the catalyst and subsequently liberated again; an alternative possibility is also to bind the catalyst by adsorption to a bed, which allows chromatographic purification to be carried out easily. It is also possible to remove the product from the catalyst by distillation.

It is possible in the intermediate conversion of the product into the carboxylate and simple precipitation thereof from the reaction mixture to increase the ee to >99.5%. Bases suitable for this are all those known to the skilled worker, with preference for amines and guanidines as neutral bases and alkoxylates, carbonates, hydroxides, oxides as metal bases. Particularly preferred metal bases are the corresponding lithium compounds.

Further preferred embodiments are described in the dependent claims and the experimental section.

EXPERIMENTAL SECTION

Example 1

Preparation of Optically Active Methylsuccinic Acid Methyl Ester (s/c 20 000/1)

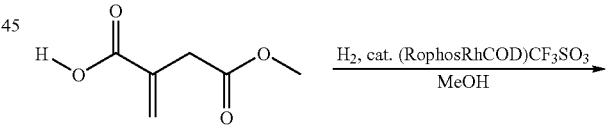

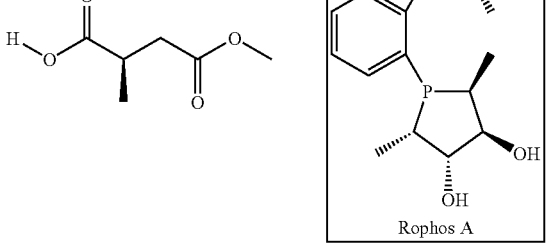

133 mg (0.182 mmol) of (RophosARhCOD)CF$_3$SO$_3$ (=precatalyst) were introduced under protective gas into 2l ml of methanol in a 4 l (enamel) Pfaudler autoclave and 526 g (3-65 mol) of 2-methylenesuccinic acid 4-monomethyl ester (=substrate) dissolved in 704 ml of methanol were added. Hydrogenation was then carried out at 40° C. under 5 bar of hydrogen. Conversion of the substrate was complete after 4 h ($^1$H-NMR, 500 MHz). The enantiomeric excess of the product (2R)-methylsuccinic acid 4-monomethyl ester was determined by gas chromatography to be >98% (from: BGB-Analytik, column type: BGB-174, length: 30 m, internal diameter: 0.25 ml, film thickness: 0.25 μm, carrier gas: helium, inlet pressure: 2.35 bar, temperature: 135° C., heating rate: 1.2° C./min, retention time of R enantiomer: 23.3 min, retention time of S enantiomer: 22.6 min). The s/c ratio was 20 000:1.

Example 2

Preparation of Optically Active Methylsuccinic Acid Methyl Ester (s/c 40 000/1)

The reaction described in example 1 was carried out with a catalyst/substrate ratio s/c of 40 000:1. Conversion of the substrate was complete after 4 h. The enantiomeric excess of the product was >98%.

Example 3

Preparation of Optically Active Methylsuccinic Acid Methyl Ester (s/c 110 000/1)

5.73 g (39.8 mmol) of 2-methylenesuccinic acid 4-monomethyl ester were introduced into 12 ml of methanol under protective gas in a 50 ml glass autoclave, and 0.12 ml of a solution of 6.6 mg of (RophosARhCOD)CF$_3$SO$_3$ (=precatalyst) in 3 ml of methanol was added (0.00036 mmol of precatalyst). Hydrogenation was then carried out at 60° C. under 5 bar of hydrogen. Conversion of the precursor was complete after 16 h. The enantiomeric excess of the product was 98%.

Example 4

Preparation of Optically Active Methylsuccinic Acid Methyl Ester on the Industrial Scale, Followed by Li Salt Formation 75 kg of methylenesuccinic acid 4-monomethyl ester (520.4 mol) were introduced into 185 l of methanol under protective gas in a 1 m$^3$ steel vessel, Addition of 19.0 g of (RophosARhCOD)CF$_8$SO$_3$ (=26 mmol of precatalyst, s/c 20 000/1) in 2 l of methanol was followed by hydrogenation at 50° C. under 4 bar of hydrogen. Conversion of the substrate was complete after 4 hours. The ee of the hydrogenation product was determined by chiral HPLC to be 99.4% (manufacturer of column: Chiracel; column type: OD-H; mobile phase: 95 vol % n-heptanel5 vol % 2-propanol-0.1 ml of trifluoroacetic acid per 1 l of this mixture; retention times:
$t_R$((R)-2-methylsuccinic acid 4-methyl ester)=7.4 min
$t_R$((S)-2-methylsuccinic acid 4-methyl ester)=16.7 min).

A total of 22.2 kg of lithium hydroxide monohydrate was added in portions, followed by 375 kg of methyl tert-butyl ether, to the reaction solution, and it was cooled to 0° C. The Li carboxylate was removed by filtration from the resulting suspension (yield: 65.8 kg). Its ee (determined after liberation) was >99.8%.

Example 5

Preparation of the Precatalyst In Situ (General Procedure)

1.1 eq of RophosA-Bistriflate salt (Rophos*2 CF$_3$SO$_3$H) are dissolved with 1.1 eq amount of base (preferably amines such as triethylamine, Hünig's base or the like) in methanol and, at −10° C., slowly added dropwise to a solution of 1 eq of the metal source, preferably (Rh[COD]$_2$)X with X=BF$_4$, CF$_3$SO$_3$, SbF$_6$, PF$_6$, ClO$_4$, BAr$_4$). The mixture is then allowed to reach room temperature. If the free ligand is used, no base is added

We claim:

1. A process for preparing optically active alkylsuccinic acid monoalkyl esters of the formula (I)

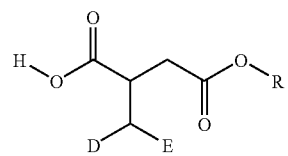

where D and E are independently of one another H, C$_1$-C$_{10}$ alkyl,
R is C$_1$-C$_{10}$ alkyl, aryl or alkylaryl,
which comprises enantioselective hydrogenating a compound of the formula (II)

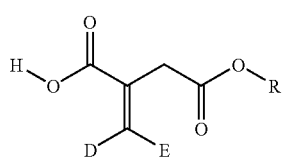

where D, E and R have the abovementioned meanings, in the presence of a catalyst that has Rh, Ru or Ir as a metal atom which includes a phospholane ligand of the formula (L)

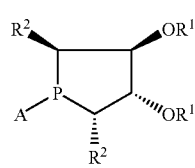

where:
R$^1$ and R$^2$ are independently of one another C$_1$-C$_6$ alkyl, aryl, alkylaryl,
R$^1$ is additionally hydrogen,
A is either R$^1$ or

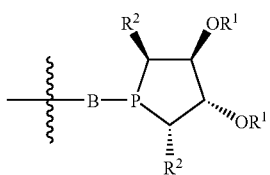

with B=a linker with 1-5 C atoms between the two P atoms or Cp-Fe-Cp.

2. The process according to claim 1, wherein D and E are hydrogen and R is Me.

3. The process according to claim 1, wherein a ligand from the group of Rophos A, Rophos B, Me-KetalPhos, Me-f-KetalPhos is used as ligand (L).

4. The process according to claim 1, wherein the hydrogenation is carried out under a pressure of between 1 and 100 bar of hydrogen.

5. The process according to claim 1, wherein the hydrogenation is carried out in methanol.

6. The process according to claim 1, wherein the hydrogenation is carried out at a temperature between 10° C. and 80° C.

7. The process according to claim 1, wherein the catalyst used is immobilized.

8. The process according to claim 1, wherein the reaction product (I) resulting from the hydrogenation is converted into a carboxylate and is removed in this form from the reaction mixture.

9. The process according to claim 8, wherein the reaction product (I) is precipitated in the form of an Li carboxylate from the reaction mixture.

10. The process as claimed in claim 1, wherein the catalyst has Rh as the metal atom.

11. The process as claimed in claim 1, wherein the catalyst has Ru as the metal atom.

12. The process as claimed in claim 1, wherein the catalyst has Ir as the metal atom.

\* \* \* \* \*